US005620675A

United States Patent [19]
McBride et al.

[11] Patent Number: 5,620,675
[45] Date of Patent: *Apr. 15, 1997

[54] RADIOACTIVE PEPTIDES

[75] Inventors: William McBride, Manchester; Richard T. Dean, Bedford, both of N.H.

[73] Assignee: Diatech, Inc., Londonderry, Ill.

[ * ] Notice: The term of this patent shall not extend beyond the expiration date of Pat. No. 5,552,525.

[21] Appl. No.: 95,760

[22] Filed: Jul. 21, 1993

Related U.S. Application Data

[63] Continuation-in-part of Ser. No. 902,935, Jun. 23, 1992.
[51] Int. Cl.$^6$ .................. A61K 38/31; A61K 38/00; A61K 51/00
[52] U.S. Cl. .................. 424/1.69; 530/500; 530/322; 530/311; 424/1.73; 424/9.3; 424/9.35; 424/9.4; 424/9.43; 424/9.6
[58] Field of Search .................. 530/311, 313, 530/303, 333, 330, 350, 326, 402, 317, 300, 322; 424/1.11, 1.1, 1.69, 1.73, 9.3, 9.35, 9.4, 9.43, 9.6

[56] References Cited

U.S. PATENT DOCUMENTS

| | | | |
|---|---|---|---|
| 4,235,886 | 11/1980 | Freidinger | 530/326 |
| 4,444,690 | 4/1984 | Fritzberg | 530/26 |
| 4,472,509 | 9/1984 | Gansow et al. | 530/326 |
| 4,485,101 | 11/1984 | Coy et al. | 530/326 |
| 4,608,251 | 8/1986 | Mia | 530/313 |
| 4,611,054 | 9/1986 | Freidinger | 530/326 |
| 4,612,366 | 9/1986 | Nutt | 530/326 |
| 4,853,371 | 8/1989 | Coy et al. | 530/326 |
| 4,871,717 | 10/1989 | Coy et al. | 530/326 |
| 4,904,642 | 2/1990 | Coy et al. | 530/326 |
| 5,073,541 | 12/1991 | Taylor et al. | 530/326 |
| 5,084,442 | 1/1992 | Felix et al. | 530/317 |
| 5,196,510 | 3/1993 | Rodwell et al. | 530/326 |
| 5,212,072 | 5/1993 | Blalock et al. | 530/333 |
| 5,225,180 | 7/1993 | Dean et al. | 530/350 |

FOREIGN PATENT DOCUMENTS

| | | |
|---|---|---|
| 83111747 | 7/1984 | European Pat. Off. |
| 85810617 | 7/1986 | European Pat. Off. |
| 87300426 | 9/1987 | European Pat. Off. |
| 90302760 | 3/1990 | European Pat. Off. |
| 90304551 | 10/1990 | European Pat. Off. |
| 911048445.2 | 10/1991 | European Pat. Off. |
| 92810381.1 | 11/1992 | European Pat. Off. |
| 8927255 | 6/1990 | United Kingdom |
| 2225579 | 6/1990 | United Kingdom |

OTHER PUBLICATIONS

Reubi et al, Chem Abstracts, 103: 135620 (1985).
Bomanji et al., 1992, "A scintigraphic comparison of iodine–123–metaiodobenzylguanidine and an iodine–labeled somatostatin analog (Tyr–3–octreotide) in metastatic carcinoid tumors", J. Nucl. Med. 33: 1121–1124.
Krenning et al., 1992, "Somatostatin receptor scintigraphy with indium–111–DTPA–D–Phe–1–octreotide in man: Metabolism, dosimetry and comparison with iodine–123–Tyr–3–octreotide", J. Nucl. Med. 33: 652–658.
Cox et al., 1991, "Technetium Labeled Somatostatin: A Potential Agent for In Vivo Tumour Localization", Abstract, 7th International Symposium on Radiopharmacology, p. 16.
Albert et al., 1991, "A Somatostatin Analogue to Image SS–Receptor–Positive Tumours: [$^{111}$In–DTPA–DPhe] $1^1$–Octreotide (SDZ 215–811)", Abstract LM10, 12th American Peptide Symposium: 1991.
Faglia et al., 1991, "In vivo detection of somatostatin receptors in patients with functionless pituitary adenomas by means of a radioiodinated analog of somatostatin ([$^{123}$I] )SDZ 204–090)", J. Clin. Endocrinol. Metab. 73: 850–856.
Larson, 1991, "Receptors on Tumors Studied with Radionuclide Scintigraphy", J. Nucl. Med. 32: 1189–1191.

Primary Examiner—John Kight
Assistant Examiner—Louise N. Leary
Attorney, Agent, or Firm—Banner & Witcoff, Ltd.

[57] ABSTRACT

This invention relates to therapeutic reagents and peptides, radiodiagnostic reagents and peptides, and methods for producing label radiodiagnostic agents. Specifically, the invention relates to linear peptide derivatives and analogs of somatostatin, and embodiments of such peptides radiolabeled with a radioisotope, as well as methods and kits for making, radiolabeling and using such peptides for radiodiagnostic and radiotherapeutic purposes. The invention specifically relates to linear peptide derivatives and analogues of somatostatin radiolabeled with technetium-99m and uses thereof as scintigraphic imaging agents. The invention so specifically relates to liner peptide derivatives and analogues of somatostatin radiolabeled with cytotoxic radioisotopes such as rhenium-186 ($^{186}$Re) and rhenium-188 ($^{188}$Re) for use as radiotherapeutic agents. Methods and kits for making, radiolabeling and using such peptides diagnostically and therapeutically in a mammalian body are also provide.

68 Claims, No Drawings

RADIOACTIVE PEPTIDES

This application is a continuation-in-part of copending U.S. patent application Ser. No. 07/902,935, filed Jun. 23, 1992.

BACKGROUND OF THE INVENTION

1. Field of the Invention

This invention relates to therapeutic agents and peptides, radiotherapeutic agents and peptides, radiodiagnostic agents and peptides, and methods for producing such labeled radiodiagnostic and radiotherapeutic agents. Specifically, the invention relates to linear peptide derivatives and analogues of somatostatin, and embodiments of such peptides labeled with gamma radiation-emitting radioisotopes such as technetium-99m (Tc-99m), as well as methods and kits for making, radiolabeling and using such peptides to image sites in a mammalian body. The invention also relates to linear peptide derivatives and analogues of somatostatin labeled with cytotoxic radioisotopes such as rhenium-186 ($^{186}$Re) and rhenium-188 ($^{188}$Re), and methods and kits for making, radiolabeling and using such peptides therapeutically in a mammalian body.

2. Decription of the Prior Art

Somatostatin is a tetradecapeptide that is endogenously produced by the hypothalamus and pancreas in humans and other mammals. The peptide has the formula:

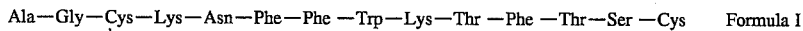

Ala—Gly—Cys—Lys—Asn—Phe—Phe—Trp—Lys—Thr—Phe—Thr—Ser—Cys   Formula I

[Single letter abbreviations for amino acids can be found in G. Zubay, *Biochemistry* (2d ed.), 1988, (MacMillan Publishing: New York), p.33]. This peptide exerts a wide variety of biological effects in vivo. It is known to act physiologically on the central nervous system, the hypothalamus, the pancreas, and the gastrointestinal tract.

Somatostatin inhibits the release of insulin and glucagon from the pancreas, inhibits growth hormone release from the hypothalamus, and reduces gastric secretions. Thus, somatostatin has clinical and therapeutic applications for the alleviation of a number of ailments and diseases, both in humans and other animals. Native somatostatin is of limited utility, however, due to its short half-life in vivo, where it is rapidly degraded by peptidases. For this reason, somatostatin analogues having improved in vivo stability have been developed in the prior art.

Freidinger, U.S. Pat. No. 4,235,886 disclose cyclic hexapeptide somatostatin analogues useful in the treatment of a number of diseases in humans.

Coy and Murphy, U.S. Pat. No. 4,485,101 disclose synthetic dodecapeptide somatostatin analogues.

Freidinger, U.S. Pat. No. 4,611,054 disclose cyclic hexapeptide somatostatin analogues useful in the treatment of a number of diseases in humans.

Nutt, U.S. Pat. No. 4,612,366 disclose cyclic hexapeptide somatostatin analogues useful in the treatment of a number of diseases in humans.

Coy et al., U.S. Pat. No. 4,853,371 disclose synthetic octapeptide somatostatin analogues.

Coy and Murphy, U.S. Pat. No. 4,871,717 disclose synthetic heptapeptide somatostatin analogues.

Coy et al., U.S. Pat. No. 4,904,642 disclose synthetic octapeptide somatostatin analogues.

Taylor et al., U.S. Pat. No. 5,073,541 disclose a method of treating small cell lung cancer.

Brady, European Patent Application No. 83111747.8 discloses dicyclic hexapeptide somatostatin analogues useful in the treatment of a number of human diseases.

Bauer et al., European Patent Application No. 85810617.2 disclose somatostatin derivatives useful in the treatment of a number of human diseases.

Eck and Moreau, European Patent Application No. 90302760.5 disclose therapeutic octapeptide somatostatin analogues.

Coy and Murphy, European Patent Application Ser. No. 90304551.6 disclose linear somatostatin analogues.

Coy and Murphy, International Patent Application Ser. No. PCT/US90/07074 disclose somatostatin analogues for therapeutic uses.

Schally et al., European Patent Application Ser. No. EPA 911048445.2 disclose cyclic peptides for therapeutic use.

Bodgen and Moreau, International Patent Application Ser. No. PCT/US92/01027 disclose compositions and methods for treating proliferative skin disease.

Somatostatin exerts it effects by binding to specific receptors expressed at the cell surface of cells comprising the central nervous system, the hypothalamus, the pancreas, and the gastrointestinal tract. These high-affinity somatostatin binding sites have been found to be abundantly expressed at the cell surface of most endocrine-active tumors arising from these tissues. Expression of high-affinity binding sites for somatostatin is a marker for these tumor cells, and specific binding with somatostatin can be exploited to locate and identify tumor cells in vivo.

Methods for radiolabeling somatostatin analogues that have been modified so as to contain a tyrosine amino acid (Tyr or Y) are known in the prior art.

Albert et al., UK Patent Application 8927255.3 disclose radioimaging using somatostatin derivatives such as octreotide labeled with $^{123}$I.

Bakker et al., 1990, J. Nucl. Med. 31: 1501–1509 describe radioactive iodination of a somatostatin analog and its usefulness in detecting tumors in vivo.

Bakker et al., 1991, J. Nucl. Med. 32: 1184–1189 teach the usefulness of radiolabeled somatostatin for radioimaging in vivo.

Bomanji et al., 1992, J. Nucl. Med. 33: 1121–1124 describe the use of iodinated (Tyr-3) octreotide for imaging metastatic carcinoid tumors.

Alternatively, methods for radiolabeling somatostatin by covalently modifying the peptide to contain a radionuclide-chelating group have been disclosed in the prior art.

Albert et al., UK Patent Application 8927255.3 disclose radioimaging using somatostatin derivatives such as octreotide labeled with $^{111}$In via a chelating group bound to the amino-terminus.

Albert et al., European Patent Application No. WO 91/01144 disclose radioimaging using radiolabeled peptides related to growth factors, hormones, interferons and cytokines and comprised of a specific recognition peptide covalently linked to a radionuclide chelating group.

Albert et al., European Patent Application No. 92810381.1 disclose somatostatin peptides having amino-terminally linked chelators.

Faglia et al., 1991, J. Clin. Endocrinol. Metab. 73: 850–856 describe the detection of somatostatin receptors in patients.

Kwekkeboom et al., 1991, J. Nucl. Med. 32: 981 Abstract #305 relates to radiolabeling somatostatin analogues with $^{111}$In.

Albert et al., 1991, Abstract LM10, 12th American Peptide Symposium: 1991 describe uses for $^{111}$In-labeled diethylene-triaminopentaacetic acid-derivatized somatostatin analogues.

Krenning et al., 1992, J. Nucl. Med. 33: 652–658 describe clinical scintigraphy using [$^{111}$In ][DTPA]octreotide.

These methods can be readily adapted to enable detection of tumor cells in vivo by radioimaging, based on the expression of high affinity binding sites for somatostatin on tumor cells. Radionuclides which emit gamma radiation can be readily detected by scintigraphy after injection into a human or an animal. A variety of radionuclides are known to be useful for radioimaging, including $^{67}$Ga, $^{68}$Ga, $^{99m}$Tc (Tc-99m), $^{111}$In, $^{123}$I or $^{125}$I. The sensitivity of imaging methods using radioactively-labeled peptides is much higher than other techniques known in the art, since the specific binding of the radioactive peptide concentrates the radioactive signal over the cells of interest, for example, tumor cells. This is particularly important for endocrine-active gastrointestinal tumors, which are usually small, slow-growing and difficult to detect by conventional methods. Labeling with technetium-99m (Tc-99m) is advantageous because the nuclear and radioactive properties of this isotope make it an ideal scintigraphic imaging agent. Tc-99m has a single photon energy of 140 keV and a radioactive half-life of about 6 hours, and is readily available from a $^{99}$Mo-$^{99m}$Tc generator. Other radionuclides have effective half-lives which are much longer (for example, $^{111}$In, which has a half-life of 60–70 h) or are toxic (for example, $^{125}$I). Although Tc-99m is an ideal radiolabeling reagent, it has not been widely used in the art prior to the present invention [see, for example, Lamberts, J. Nucl. Med. 32: 1189–1191 (1991)].

Somatostatin and radiolabeled somatostatin analogues can also be used therapeutically. For these applications, cytotoxic radioisotopes are advantageous, such as scandium-47, copper67, gallium-72, yttrium-90, iodine-125, iodine-131, samarium-153, gadolinium-159, dysprosium-165, holmium-166, ytterbium-175, lutetium-177, rhenium-186, rhenium-188, astatine-211, and bismuth-212. The rhenium isotopes $^{186}$Re and $^{188}$Re are particularly advantageous.

The use of chelating agents for radiolabeling proteins are known in the prior art, and methods for labeling peptides Tc-99m are disclosed in U.S. patent application Ser. Nos. 07/653,012 filed Feb. 8, 1991, now abandoned; 07/757,470 filed Sep. 10, 1991, now U.S. Pat. No. 5,225,180; 07/807,062 filed Nov. 27, 1991, now U.S. Pat. No. 5,443,815; 07/851,074 filed Mar. 13, 1992, now abandoned; 07/886,752 filed May 21, 1992, now abandoned; 07/893,981 filed Jun. 5, 1992, now U.S. Pat. No. 5,508,020; 07/955,466 filed Oct. 2, 1992, now abandoned; 07/977,628 filed Nov. 17, 1992, now U.S. Pat. No. 5,405,597; 08/044,825 filed Apr. 8, 1993, now abandoned; and co-pending application Ser. Nos. 07/871,282 filed Apr. 30, 1992; 08/019,864 filed Feb. 19, 1993; and Ser. No. 08/073,577 filed Jun. 7, 1993 and PCT International Applications PCT/US92/00757, PCT/US92/10716, PCT/US93/02320, PCT/US93/03687, PCT/US93/04794, and PCT/US93/06029, which are hereby incorporated by reference.

Fritzberg, U.S. Pat. No. 4,444,690 describes a series of technetium-chelating agents based on 2,3-bis(mercaptoacetamido) propanoate.

Gansow et al., U.S. Pat. No. 4,472,509 teach methods of manufacturing and purifying Tc-99m chelate-conjugated monoclonal antibodies.

Reno and Bottino, European Patent Application 87300426.1 disclose radiolabeling antibodies with Tc-99m.

Pak et al., European Patent Application No. WO 88/07382 disclose a method for labeling antibodies with Tc-99m.

Cox, International Patent Application No. PCT/US92/04559 discloses radiolabeled somatostatin derivatives containing two cysteine residues.

Rhodes, 1974, Sem. Nucl. Med. 4: 281–293 teach the labeling of human serum albumin with technetium-99m.

Khaw et al., 1982, J. Nucl. Med. 23: 1011–1019 disclose methods for labeling biologically active macromolecules with Tc-99m.

Byrne and Tolman, supra, disclose a bifunctional thiolactone chelating agent for coupling Tc-99m to biological molecules.

Cox et al., 1991, Abstract, 7th International Symposium on Radiopharmacology, p. 16, disclose the use of, Tc-99m-, $^{131}$I- and $^{111}$In-labeled somatostatin analogues in radiolocalization of endocrine tumors in vivo by scintigraphy.

Methods for directly labeling somatostatin, derivatives of somatostatin, analogues of somatostatin or peptides that bind to the somatostatin receptor and contain at least 2 cysteine residues that form a disulfide or wherein the disulfide is reduced to the sulfhydryl form, are disclosed in co-pending U.S. patent application Ser. No. 07/807,062, filed Nov. 27, 1991, now U.S. Pat. No. 5,443,815 which is hereby incorporated by reference.

There remains a need for synthetic (to make routine manufacture practicable and to ease regulatory acceptance) somatostatin analogues having increased in vivo stability, to be used therapeutically, as scintigraphic agents when radiolabeled with Tc-99m or other detectable radioisotopes for use in imaging tumors in vivo, and as radiotherapeutic agents when radiolabeled with a cytotoxic radioisotope such as rhenium-188. Small synthetic somatostatin analogues are provided by this invention that specifically fulfill this need.

SUMMARY OF THE INVENTION

The present invention provides somatostatin analogues that are linear peptides for therapeutic applications, including radiotherapeutic applications, and diagnostic applications, including radiodiagnostic applications, in particular scintigraphic imaging applications. Distinct from native somatostatin and somatostatin analogues known in the prior art, the linear peptides of the invention are not constrained within a cyclic structure. The invention also provides linear peptide reagents comprised of the linear peptide somatostatin analogues of the invention, wherein such peptides are covalently linked to a radiolabel-binding moiety. The invention provides such linear peptides, linear peptide reagents and radiolabeled linear peptide reagents that are scintigraphic imaging agents, radiodiagnostic agents and radiotherapeutic agents. Scintigraphic imaging agents of the invention comprise linear peptide reagents radiolabeled with a radioisotope, preferably technetium-99m. Radiotherapeutic agents of the invention comprise linear peptide reagents radiolabeled with a cytotoxic radioisotope, preferably rhenium-186 or rhenium-188. Methods for making and using such linear peptides, linear peptide reagents and radiolabeled embodiments thereof are also provided.

The present invention also provides scintigraphic imaging agents comprised of a linear peptide that is a somatostatin analogue and that is labeled with iodine-123, iodine-125 or iodine-131. Similarly, the invention provides alternative embodiments of the linear somatostatin peptide analogues radiolabeled with iodine-125, iodine-131 or astatine-211 for use as therapeutic agents.

The somatostatin analogues provided by the invention are somatostatin-receptor binding peptides having the following formula:

$$X^1-A^1A^2-B^1B^2B^3B^4-C^1C^2-X^2 \quad \text{(Formula II)}$$

wherein $X^1$ is a hydrophilic moiety which is not greater than 1500 Daltons in formula weight; $A^1$, $A^2$ and $C^1$ are each independently a lipophilic D- or L-amino acid, S-alkylated cysteine, penicillamine (Pen), homocysteine (Hcy) or homo-homocysteine (Hhc; 3-mercaptopropyl) glycine; $B^1$ is D- or L-Phe, or D- or L-Tyr, or D- or L-2-naphthylalanine (Nal), or 2-amino-indane-2-carboxylic acid (Ain) or substituted derivatives thereof; $B^2$ is D- or L-Trp or substituted derivatives thereof; $B^3$ is D- or L-Lys, or homolysine (Hly), 4-aminocyclohexylalanine (Achxa), 4-aminomethyl-phenylalanine (Amf), S-(2-aminoethyl)cysteine (Aec), S-(3-aminopropyl)cysteine (Apc), O-(2-aminoethyl) serine (Aes), O-(3-aminopropyl)serine (Aps) or substituted derivatives thereof; $B^4$ is Thr, Ser, Val, Phe, Leu, Ile, 2-amino-isobutyric acid (Aib), 2-aminobutyric acid (Abu), norvaline (Nva), or norleucine (Nle); $C^2$ is D- or L-Thr, Ser, Val, Phe, Ile, Abu, Nle, Leu, Nva, Nal or Aib or substituted derivatives thereof; $X^2$ is a hydrophilic moiety which is not more than 1500 Daltons in formula weight. In a preferred embodiment, $X^1$ is a hydrophilic moiety that comprises an amino acid, or a peptide having an amino acid sequence of no more than 10 residues, or a monosaccharide, or an oligosaccharide comprising 10 or fewer saccharide units, or a poly(N-carboxyalkyl)amine, or a polyoxyanion. In another preferred embodiment, $X^2$ is a hydrophilic moiety that comprises a poly(N-carboxyalkyl)amine or polyoxyanion, or an amino acid, or a peptide having an amino acid sequence of no more than 10 residues (including peptides wherein the carboxyl group of the carboxyl-terminal amino acid is reduced to an alcohol), or a monosaccharide or an oligosaccharide comprising 10 or fewer saccharide units. In another preferred embodiment, $B^1$ is phenylalanine or tyrosine, $B^2$ is tryptophan, most preferably D-tryptophan, $B^3$ is lysine and $B^4$ is threonine or valine.

The invention also provides linear peptide reagents comprising a linear peptide of Formula II covalently linked to a radiolabel-binding moiety, wherein $X^1$ is H, lower alkyl or substituted alkyl, aryl or substituted aryl, alkanoyl or substituted alkanoyl, aroyl or substituted aroyl, or a hydrophilic moiety which is not greater than 1500 Daltons in formula weight; $A^1$, $A^2$ and $C^1$ are each independently a lipophilic D- or L-amino acid, S-alkylated cysteine, penicillamine (Pen), homocysteine (Hcy) or homohomocysteine (Hhc; 3-mercaptopropyl) glycine; $B^1$ is D- or L-Phe, or D- or L-Tyr, or D- or L-2-naphthylalanine (Nal), or 2-amino-indane-2-carboxylic acid (Ain) or substituted derivatives thereof; $B^2$ is D-or L-Trp or substituted derivatives thereof; B3 is D- or L-Lys, or homolysine (Hly), 4-aminocyclohexylalanine (Achxa), 4-aminomethyl-phenylalanine (Amf), S-(2-aminoethyl)cysteine (Aec), S-(3-aminopropyl)cysteine (Apc), O-(2-aminoethyl) serine (Aes), O-(3-aminopropyl)serine (Aps) or substituted derivatives thereof; $B^4$ is Thr, Set, Val, Phe, Leu, Ile, 2-amino-isobutyric acid (Aib), 2-aminobutyric acid (Abu), norvaline (Nva), or norleucine (Nle); $C^2$ is D- or L-Thr, Ser, Val, Phe, Ile, Abu, Nle, Leu, Nva, Nat or Aib or substituted derivatives thereof; $X^2$ is —COOR$^9$, —CH$_2$OH, CH$_2$COOR$^9$, or —CON(R$^9$)$_2$, where each R$^9$ is independently H, lower linear or cyclic alkyl or substituted derivatives thereof, or substituted with a hydrophilic moiety which is not more than 1500 Daltons in formula weight. In a preferred embodiment, when Xis a hydrophilic moiety that moiety comprises an amino acid, or a peptide having an amino acid sequence of no more than 10 residues, or a monosaccharide, or an oligosaccharide comprising 10 or fewer saccharide units, or a poly(N-carboxyalkyl)amine, or a polyoxyanion. In another preferred embodiment, when $X^2$ is a hydrophilic moiety that moiety comprises a poly(N-carboxyalkyl)amine or polyoxyanion, or an amino acid, or a peptide having an amino acid sequence of no more than 10 residues (including peptides wherein the carboxyl group of the carboxyl-terminal amino acid is reduced to an alcohol), or a monosaccharide or an oligosaccharide comprising 10 or fewer saccharide units. In another preferred embodiment, Bis phenylalanine or tyrosine, $B^2$ is tryptophan, most preferably D-tryptophan, $B^3$ is lysine and $B^4$ is threonine or valine.

The present invention provides peptides that are linear somatostatin peptide analogues as described herein having increased in vivo stability compared with native somatostatin, and that are therapeutically useful in the alleviation of diseases or other ailments in humans or other animals.

The invention also provides scintigraphic imaging agents comprising the linear peptide reagents of the invention wherein the radiolabel-binding moiety is stably complexed with a radioisotope. In one such embodiment is provided a scintigraphic imaging agent wherein the linear somatostatin peptide analogue reagents of the invention are radiolabeled with technetium-99m. In other embodiments of the scintigraphic imaging agents of the invention the radioisotope is indium-111 or gallium-68. In still other embodiments, the scintigraphic imaging agents of the invention are linear peptides that are radiolabeled with iodine-123 or iodine-125.

The invention also provides radiotherapeutic agents that are the linear peptide reagents of the invention radiolabeled with a cytotoxic radioisotope that is selected from the group consisting of scandium-47, copper-67, gallium-72, yttrium-90, iodine-125, iodine-131, samarium-153, gadolinium-159, dysprosium-165, holmium-166, ytterbium-175, lutetium-177, rhenium-186, rhenium-188,astatine-211 and bismuth-212. In preferred embodiments, the radioisotope is rhenium-186 or rhenium-188. In additional preferred embodiments, the cyclic peptides of the invention are radiolabled with iodine-125, iodine-131 or astatine-211.

In another embodiment, the invention provides therapeutic agents comprising the linear spmatostain analogue peptide reagents of the invention complexed with a non-radioactive metal such as rhenium. Combination embodiments, wherein such a complex is also radiolabeled, either directly or via a radiolabel-binding moiety, are also provided by the invention and are within its scope.

The invention also provides pharmaceutical compositions comprising the somatostatin receptor-binding peptides of the invention in a pharmaceutically acceptable carrier.

The invention also provides a method for alleviating somatostatin-related diseases in animals, preferably humans, comprising administering a therapeutically effective amount of the somatostatin analogues of the invention to the animal. In preferred embodiments, the amount of the somatostatin analogue administered is from about 0.1 to about 50 mg/kg body weight/day.

It is an advantage of the somatostatin analogues provided by this invention that the peptides retain high affinity for somatostatin receptors even though they are linear peptides. As the preferred embodiments lack intramolecular disulfide bonding, the advantageous feature of the linear somatostatin peptide analogues of this invention is that their stability is not dependent on the formation or persistence of intramolecular disulfide bonds. This feature is in turn advantageous because the high affinity of the peptides of this invention for somatostatin receptors is thus not a function of the integrity of labile intramolecular crosslinks such as disulfide bonds. Additionally, the peptide reagents of the invention retain their high affinity for somatostatin receptors after being subjected to radiolabeling via covalently-linked radiolabeled binding moieties. In contrast, for example, Tc-99m conjugation to a Tc-99m binding moiety covalently linked to native somatostatin, or to a somatostatin analogue having a disulfide bond, can result in reduction of the disulfide accompanied by a loss of biological activity. Such loss of biological activity can also occur in vivo using native somatostatin, or to any somatostatin analogue having a disulfide bond. The present invention is not subject to similar losses in biological activity in vivo because the somatostatin analogues of the invention are active as linear peptides.

A first aspect of the reagents provided by the invention for preparing radiolabeled agents of the invention are reagents, each comprised of a peptide that is a somatostatin analogue that is covalently linked to a radiolabel-binding moiety having formula:

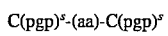

wherein $(pgp)^s$ is H or a thiol protecting group and (aa) is an amino acid. In a preferred embodiment, the amino acid is glycine. In another preferred embodiment, the agent is a scintigraphic imaging agent. In yet another preferred embodiment, the agent is a radiotherapeutic agent.

In a second embodiment, the invention provides peptide reagents capable of being radiolabeled for use as scintigraphic imaging agents or radiotherapeutic agents, each comprising a somatostatin analogue that is covalently linked to a radiolabel-binding moiety of formula:

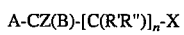

wherein A is H, HOOC, $H_2NOC$, (peptide)-NHOC, (peptide)-OOC or R''''; B is H, SH or —NHR''', —N(R''')-(peptide) or R''''; X is SH or —NHR''', —N(R''')-(peptide) or R''''; Z is H or R''''; R', R'', R''' and R'''' are independently H or straight or branched chain or cyclic lower alkyl; n is 0, 1 or 2; and: (1) where B is —NHR''' or —N(R''')-(peptide), X is SH and n is 1 or 2; (2) where X is —NHR''' or —N(R''')-(peptide), B is SH and n is 1 or 2; (3) where B is H or R'''', A is HOOC, $H_2NOC$, (peptide)-NHOC, (peptide)-OOC, X is SH and n is 0 or 1; (4) where A is H or R'''', then where B is SH, X is —NHR''' or —N(R''')-(peptide) and where X is SH, B is —NHR''' or —N(R''')-(peptide); (5) where X is H or R'''', A is HOOC, $H_2NOC$, (peptide)-NHOC, (peptide)-OOC and B is SH; (6) where Z is methyl, X is methyl, A is HOOC, $H_2NOC$, (peptide)-NHOC, (peptide)-OOC and B is SH and n is 0; and (7) where Z is SH and X is SH, n is not 0; and wherein the thiol moiety is in the reduced form.

In another embodiment, the invention provides peptide reagents capable of being radiolabeled with a radioisotope, for radiotherapy or for imaging sites within a mammalian body, each comprising a somatostatin anal. ogue that is covalently linked to a radiolabelbinding moiety of formula:

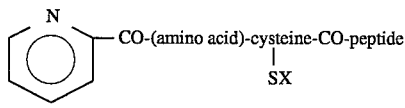

[for purposes of this invention, radiolabel-binding moieties having this structure will be referred to as picolinic acid (Pic)-based moieties] or

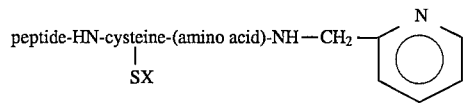

wherein X is H or a protecting group; (amino acid) is any amino acid and the radiolabel-binding moiety is covalently linked to the peptide. For purposes of this invention, radiolabel-binding moieties having this structure will be referred to as picolylamine (Pica)-based moieties. In a preferred embodiment, the amino acid is glycine and X is an acetamidomethyl protecting group.

Yet another embodiment of the invention provides peptide reagents capable of being radiolabeled with a radioisotope, for imaging sites within a mammalian body or for use as a radiotherapeutic agent, each comprising a somatostatin analogue that is covalently linked to a radiolabel-binding moiety that is a bisamino bisthiol radiolabel-binding moiety. The bisamino bisthiol radiolabel-binding moiety in this embodiment of the invention has the formula:

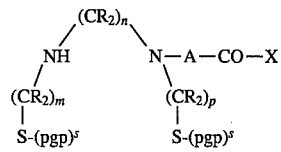

wherein each R can be independently H, $CH_3$ or $C_2H_5$; each $(pgp)^s$ can be independently a thiol protecting group or H; m, n and p are independently 2 or 3; A is linear or cyclic lower alkyl, aryl, heterocyclyl, combinations or substituted derivatives thereof; and X is peptide; or

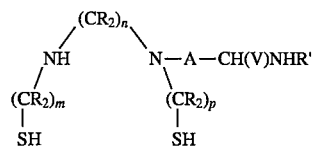

wherein each R is independently H, $CH_3$ or $C_2H_5$; m, n and p are independently 2 or 3; A is linear or cyclic lower alkyl, aryl, heterocyclyl, combinations or substituted derivatives thereof; V is H or CO-peptide; R' is H or peptide; provided that when V is H, R' is peptide and when R' is H, V is CO-peptide. For purposes of this invention, radiolabel-binding moieties having these structures will be referred to as "BAT" moieties.

This invention provides methods for preparing peptide reagents of the invention by chemical synthesis in vitro. In a preferred embodiment, peptides are synthesized by solid phase peptide synthesis.

This invention provides reagents for preparing a radiolabled somatostatin receptor-binding agent comprising the somatostatin receptor-binding peptides of the invention covalently linked to a radiolabel-binding moiety. In a preferred embodiment, the reagent is radioactively labeled with Tc-99m. In another preferred embodiment, the reagent is radioactively labeled with [186]Re or [188]Re.

The invention also provides complexes of the linear peptide reagents of the invention with a radioisotope, as well as methods for radiolabeling the peptide reagents of the invention. For example, in one embodiment scintigraphic imaging agents provided by the invention comprise Tc-99m labeled complexes formed by reacting the peptide reagents of the invention with Tc-99m in the presence of a reducing agent. Preferred reducing agents include but are not limited to dithionite ion, stannous ion and ferrous ion. Such Tc-99m complexes of the invention are also formed by labeling the peptide reagents of the invention with Tc-99m by ligand exchange of a prereduced Tc-99m complex as provided herein.

The invention also provides kits for preparing radiolabeled linear somatostatin analogue peptides from the peptide reagents of the invention. Kits for radiolabeling the peptide reagents of the invention are comprised of a sealed vial containing a predetermined quantity of a peptide reagent of the invention and a sufficient amount of reducing agent to radiolabel the peptide. In a preferred embodiment, the radiolabeled somatostain analogue is a scintigraphic imaging agent. Also preferred is radiolabeling the peptide reagents of the invention with Tc-99m. Kits for preparing radiotheapeutic agents are also provided, wherein the preferred radioisotopes are rhenium-186 and rhenium-188.

This invention provides methods for using the radiolabeled peptide reagents of the invention diagniostically and therapeutically. In one embodiment of the invention, methods are provided for using scintigraphic imaging agents that are Tc-99m labeled peptide reagents for imaging sites within a mammalian body by obtaining in vivo gamma scintigraphic images. These methods comprise administering an effective diagnostic amount of Tc-99m labeled peptide reagents of the invention and detecting the gamma radiation emitted by the Tc-99m label localized at the site within the mammalian body.

The invention also provides methods for alleviating somatostatin-related diseases in animals, preferably humans, comprising administering a therapeutically effective amount of the radiolabeled somatostatin-binding peptide reagents of the invention to the animal. In preferred embodiments, the reagent is radioactively labeled with $^{186}$Re or $^{188}$Re.

The peptides and peptide reagents of the invention may also be comprised of a polyvalent linking moiety. Polyvalent linking moieties of the invention are comprised of at least 2 identical linker functional groups capable of covalently bonding to somatostatin analogue peptides or Tc-99m binding moieties. Preferred linker functional groups are primary or secondary amines, hydroxyl groups, carboxylic acid groups or thiol-reactive groups. In preferred embodiments, the polyvalent linking moieties are comprised of bis-succinimidylmethylether (BSME), 4-(2,2-dimethylacetyl)benzoic acid (DMBA), N-[2-(N',N'-bis (2-succinimido-ethyl)amino-ethyl)]-N$^6$,N$^9$-bis(2-methyl-2-mercaptopropyl)-6,9-diazanonanamide (BAT—BS), tris(succinimidylethyl)amine (TSEA), bis-succinimidohexane (BSH), 4-(O-CH$_2$CO-Gly-Gly-Cys.amide)-2-methylpropiophenone (ETAC) or a derivative thereof.

Specific preferred embodiments of the present invention will become evident from the following more detailed description of certain preferred embodiments and the claims.

DETAILED DESCRIPTION OF THE INVENTION

The present invention provides linear peptide reagents for preparing radiolabeled agents for radiodiagnostic and radiotherapeutic uses. The present invention provides linear peptides that are somatostatin analogues and that are not not constrained within a cyclic structure. Such somatostatin analogues thereby possess increased in vivo stability compared with native somatostatin. These linear peptides are themselves therapeutic agents for alleviating diseases and other ailments in animals including humans.

Also provided by the invention are linear peptides that may be radioiodinated or radioastatinated and which are thereby useful in radiotherapeutic and radiodiagnostic applications.

Another embodiment of these linear peptides that is provided by this invention are linear peptide reagents wherein the linear peptides of the invention are covalently linked to a radiolabel-binding moiety. Such linear peptide reagents are capable of being radiolabeled to provide radiodiagnostic or radiotherapeutic agents. One example of a radiodiagnostic application using the radiolabeled agents of the invention is scintigraphic imaging, wherein the location and extent of somatostatin receptor-bearing tumors may be determined.

The linear peptide reagents of the invention can also advantageously be radiolabeled with cytotoxic radioisotopes such as rhenium-186 or rhenium-188 for radiotherapeutic uses. The linear peptide reagents of the invention are also useful in preparing complexes with nonradioactive metals, said complexes being useful therapeutically.

The invention provides a method for using the somatostatin analogues of the invention to alleviate diseases or other ailments in animals, preferably humans. These diseases and ailments include but are not limited to diabetes and diabetes-related retinopathy, cirrhosis of the liver and hepatitis infection, bleeding ulcers and other gastrointestinal bleeding, pancreatitis, central nervous system disorders, endocrine disorders, Alzheimer's disease, acromegaly and other diseases and disorders related to the production of inappropriate levels of growth hormone in vivo, and cancer, particularly those cancers whose growth is dependent or influenced by growth hormone production. Dosages of the somatostatin analogues provided by the invention may be the same as those dosages of native somatostatin routinely used for treatment of the above or other diseases, or less of the compounds of the invention may be administered due to their longer in vivo half-life.

In embodiments of the invention useful as scintigraphic imaging agents, labeling with Tc-99m is an advantage of the present invention because the nuclear and radioactive properties of this isotope make it an ideal scintigraphic imaging agent. This isotope has a single photon energy of 140 keV and a radioactive half-life of about 6 hours, and is readily available from a $^{99}$Mo-$^{99m}$Tc generator. Other radionuclides may also be used in the practice of the invention as disclosed herein.

Radiotherapeutic embodiments of the invention, on the other hand, are advantageously labeled with cytotoxic radioisotopes including but not limited to scandium-47, copper-67, gallium-72, yttrium-90, iodine-125, iodine-131, samarium-153, gadolinium-159, dysprosium165, holmium-166, ytterbium-175, lutetium-177, rhenium-186, rhenium-188, astatine-211 and bismuth-212, most preferably $^{186}$Re or $^{188}$Re. Such embodiments are useful in the treatment of somatostatin-related diseases or other ailments in animals, preferably humans, including but not limited to cancer and other diseases characterized by the growth of malignant or benign tumors capable of binding somatostatin or somatostatin analogues via the expression of somatostatin receptors on the cell surface of cells comprising such tumors.

In the radiolabel-binding moieties and linear peptides covalently linked to such moieties that contain a thiol covalently linked to a thiol protecting groups [(pgp)$^5$] provided by the invention, the thiol-protecting groups may be the same or different and may be but are not limited to:

—CH$_2$—aryl (aryl is phenyl or alkyl or alkyloxy substituted phenyl);

—CH—(aryl)$_2$, (aryl is phenyl or alkyl or alkyloxy substituted phenyl);

—C—(aryl)$_3$,(aryl is phenyl or alkyl or alkyloxy substituted phenyl);

—CH$_2$—(4-methoxyphenyl);

—C(CH$_3$)$_3$

—CH—(4-pyridyl)(phenyl)$_2$;

9-phenylfluorenyl;

—CH$_2$NHCOR (R is unsubstituted or substituted alkyl or aryl);

—CH$_2$—NHCOOR (R is unsubstituted or substituted alkyl or aryl);

—CONHR (R is unsubstituted or substituted alkyl or aryl);

CH$_2$—S—CH$_2$-phenyl

Preferred protecting groups have the formula —CH$_2$—NHCOR wherein R is a lower alkyl having 1 and 8 carbon atoms, phenyl or phenyl-substituted with lower alkyl, hydroxyl, lower alkoxy, carboxy, or lower alkoxycarbonyl. The most preferred protecting group is an acetamidomethyl group.

Each somatostatin receptor-binding linear peptide-containing embodiment of the invention is comprised of a sequence of amino acids. The term amino acid as used in this invention is intended to include all L- and D- amino acids, naturally occurring and otherwise. Reagents comprising somatostatin receptor-binding peptides provided by the invention include but are not limited to the following illustrative examples of the peptide embodiments of the invention:

C$_{Acm}$GC$_{Acm}$GGGF$_D$.Cpa.YW$_D$KTFT.amide
[DTPA].F$_D$.Cpa.YW$_D$KTFT($\epsilon$-K)GC.amide
maGGGF$_D$.Cpa.YW$_D$KTFT.amide
Ac.C$_{Acm}$GC$_{Acm}$F$_D$.Cpa.YW$_D$KTFT.amide
F$_D$.Cpa.YW$_D$KTFTC$_{Acm}$GC$_{Acm}$.amide
[DTPA].D-Nal.Cpa.YW$_D$KTFT($\epsilon$-K)GCKK.amide
AKCGGGF$_D$.Cpa.YW$_D$KTFT.amide
[DTPA]D-Nal.Cpa.YW$_D$KTFT($\epsilon$-K)GC.amide
F$_D$.Cpa.YW$_D$KTFT.GGGC$_{Acm}$GC$_{Acm}$.amide
[DTPA].Aca.F$_D$.Cpa.YW$_D$KTFT($\epsilon$-K)GC.amide
[DTPA].($\epsilon$-K)GCF$_D$.FYW$_D$KTFT.amide
Ac.CGCF$_D$.Cpa.YW$_D$KTFT.amide
F$_D$.Cpa.YW$_D$KTFTCGC.amide
[DTPA].(D-Nal.CYW$_D$KVCT)$_2$
Ac.F$_D$.FYW$_D$KTFT($\epsilon$-K)GC.amide
Ac.F$_D$FYW$_D$KTFTGGG($\epsilon$-K)GC.amide
F$_D$.Cpa.YW$_D$KTC.Nal.amide
K(BAT).D-Nal.C$_{Me}$YW$_D$KVC$_{Me}$T.amide
Ac.F$_D$FYW$_D$KTFGGG($\epsilon$-K)KC.amide
Pic.GC$_{Acm}$GGGF$_D$.Cpa.YW$_D$KTFT.amide
[DTPA].D-Nal.CYW$_D$KVCT.amide
(2-ketogulonyl)D-NalFYW$_D$KVCT.amide
F$_D$.Cpa.YW$_D$K.Abu.Nal.T($\epsilon$-K)GC.amide
[DTPA].K(BAT).D-Nal.C$_{Me}$YW$_D$KVC$_{Me}$T.amide
F$_D$.Cpa.YW$_D$KTFT($\epsilon$-K)GC.amide
[DTPA].F$_D$FYW$_D$KTFT($\epsilon$-K)GC.amide
AF$_D$CFW$_D$KTC$_{Me}$T(CH$_2$OH)
[DTPA].F$_D$GYW$_D$KTCT(CH$_2$OH)
[DTPA].Nal.SYW$_D$KVT.K(BAT).amide
[DTPA].Nal.SYW$_D$KVCT.amide As used herein, the following amino acids and amino acid analogues are intended to be represented by the following abbreviations: Ac is an acetyl group; ma is mercaptoacetic acid group; Aca is 6-aminocaproic acid; Hcy is homocysteine; Hhc is homohomocysteine, which is (3-mercaptopropyl)glycine; Pen is penicillamine; Mob is the sulfhydryl protecting group 4-methoxybenzyl; Acm is the sulfhydryl protecting group acetamidomethyl; Aib is aminoisobutyric acid; Nal is 2-naphthylalanine; Ain is 2-amino-indan-2-carboxylic acid; Hly is homolysine; Achxa is 4-aminocyclohexylalanine; Amf is 4-aminomethylphenylalanine; Aec is S-(2-aminoethyl)cysteine; Ape is S-(3-aminopropyl)cysteine; Aes is O-(2-aminoethyl)serine; Aps is O-(3-aminopropyl)serine; Abu is 2-aminobutyric acid; Nva is norvaline; Aca is 6-aminocaproic acid; F$_D$ is D-phenylalanine; W$_D$ is D-tryptophan; Y$_D$ is D-tyrosine; Cpa is L-(4-chlorophenyl)alanine; Thp is 4-amino-tetrahydrothiopyran-4-carboxylic acid; D-Nal is D-2-naphthylalanine; Dpg is dipropylglycine; and Nle is norleucine. All naturally-occurring amino acids are abbreviated using standard abbreviations (which can be found in G. Zubay, *Biochemistry* (2d. ed.), 1988 (MacMillen Publishing: New York) p.33. for the purposes of this invention, the naturally-occuring amino acids are characterized as lipophilic (alanine, isoleucine, leucine, methionine, phenylalanine, proline, tryptophan and valine, as well as S-alkylated derivatives of cysteine), hydrophilic (asparagine, glutamine, threonine, serine), acidic (glutamic acid and aspartic acid), basic (arginine, histidine and lysine). T(CH$_2$OH) represents a threoninol residue, wherein the carboxyl group of the amino acid is reduced to a primary alcohol, incorporated into the peptide using the procedure of Neugebauer et al. (1990, *Peptides: Proceedings of the 11th American Peptide Symposium*, pp. 1020–21). $\epsilon$-K is intended to represent a covalent linkage via the $\epsilon$-amino group on the sidechain of a lysine residue. Pic is picolinoyl (pyridine-2-carbonyl); Pica is picolylamine (2-(aminomethyl)pyridine); [BAT] represents N$^6$,N$^9$-bis(2-mercapto-2-methylpropyl)-6,9-diazanonanoic acid; K(BAT) and Lys(BAT) represent the amino acid lysine, acylated at the $\epsilon$-amino group on the amino acid sidechain to [BAT]; [BAM] is (N$^1$,N$^4$-bis(2-mercapto-2-methylpropyl)-1,4,10-triazadecane; [BAT-BM] is N-[2-(N',N'-bis(2-maleimidoethyl) aminoethyl]-N$^9$-(t-butoxycarbonyl)-N$^6$,N$^9$-bis(2-methyl-2-triphenylmethylthiopropyl)-6,9-diazanonanamide; [BAT-BS]is N-[2-(N',N'-bis(2-succinimidethy)aminethy]-N$^6$, N$^9$-bis(2-mercapto 2-methypropyl)-6,9-diazannanamide; [BMME] is bis-maleimidomethylether; [BSME] is bis-succinimidomethylether; and [DTPA] is diethylenetriaminepentaacetic acid.

For the purposes of this invention the term "poly(N-carboxyalkyl)amine" in intended to describe a series of compounds exemplified by nitrilotriacetic acid, iminodiacetic acid, ethylenediaminetetraacetic acid (EDTA) and diethylenetriaminepentaacetic acid (DTPA).

For the purposes of this invention the term "polyoxyanion" is intended to encompass sulfates, phosphates, sulfonates, phosphonates and like compounds.

Linear somatostatin analogue peptides of the present invention can be chemically synthesized in vitro. Peptides of the present invention can generally advantageously be prepared on a peptide synthesizer. The peptides of this invention can be synthesized wherein the radiolabel-binding moiety is covalently linked to the peptide during chemical synthesis in vitro, using techniques well known to those with skill in the art. Such peptides covalently-linked to the radiolabel-binding moiety during synthesis are advantageous because specific sites of covalent linkage can be determined.

Radiolabel binding moieties of the invention may be introduced into the target linear somatostatin analogue peptides during peptide synthesis. For embodiments comprising picolinic acid [(Pic-); e.g., Pic-Gly-Cys(protecting group)-], the radiolabel-binding moiety can be synthesized as the last (i.e., amino-terminal) residue in the synthesis. In addition, the picolinic acid-containing radiolabel-binding moiety may be covalently linked to the ε-amino group of lysine to give, for example, αN(Fmoc)-Lys-εN[Pic-Gly-Cys(protecting group)], which may be incorporated at any appropriate position in the peptide chain. This sequence is particularly advantageous as it affords an easy mode of incorporation into the target somatostatin analogue peptide.

Similarly, the picolylamine (Pica)-containing radiolabel-binding moiety [-Cys(protecting group)-Gly-Pica] can be prepared during peptide synthesis by including the sequence [-Cys(protecting group)-Gly-] at the carboxyl terminus of the peptide chain. Following cleavage of the peptide from the resin the carboxyl terminus of the peptide is activated and coupled to picolylamine. This synthetic route requires that reactive side-chain functionalities remain masked (protected) and do not react during the conjugation of the picolylamine.

This invention also provides small linear synthetic peptides that are somatostatin analogues and incorporate bisamine bisthiol (BAT) chelators that may be labeled with Tc-99m.

This invention provides for the incorporation of these chelators into virtually any position in the peptide, via covalently linkage to any appropriate functional group of the peptide, except that the chelating moieties of the invention are not covalently linked to functional groups comprising the amino acid side chains of the amino acids $B^1$, $B^2$, $B^3$ or $B^4$.

In forming a complex of radioactive technetium with the reagents of this invention, the technetium complex, preferably a salt of Tc-99m pertechnetate, is reacted with the reagent in the presence of a reducing agent. Preferred reducing agents are dithionite, stannous and ferrous ions; the most preferred reducing agent is stannous chloride. Means for preparing such complexes are conveniently provided in a kit form comprising a sealed vial containing a predetermined quantity of a reagent of the invention to be labeled and a sufficient amount of reducing agent to label the reagent with Tc-99m. Alternatively, the complex may be formed by reacting a reagent of this invention with a pre-formed labile complex of technetium and another compound known as a transfer ligand. This process is known as ligand exchange and is well known to those skilled in the art. The labile complex may be formed using such transfer ligands as tartrate, citrate, gluconate or mannitol, for example. Among the Tc-99m pertechnetate salts useful with the present invention are included the alkali metal salts such as the sodium salt, or ammonium salts or lower alkyl ammonium salts.

In a preferred embodiment of the invention, a kit for preparing technetium-labeled peptides is provided. An appropriate amount of the peptide reagent is introduced into a vial containing a reducing agent, such as stannous chloride, in an amount sufficient to label the peptide with Tc-99m. An appropriate amount of a transfer ligand as described (such as tartrate, citrate, gluconate or mannitol, for example) can also be included. The kit may also contain conventional pharmaceutical adjunct materials such as, for example, pharmaceutically acceptable salts to adjust the osmotic pressure, buffers, preservatives and the like. The components of the kit may be in liquid, frozen or dry form. In a preferred embodiment, kit components are provided in lyophilized form.

Technetium-99m labeled imaging reagents according to the present invention may be prepared by the addition of an appropriate amount of Tc-99m or Tc-99m complex into the vials and reaction under conditions described in Example 2 hereinbelow.

Radioactively-labeled scintigraphic imaging agents provided by the present invention are provided having a suitable amount of radioactivity. In forming Tc-99m radioactive complexes, it is generally preferred to form radioactive complexes in solutions containing radioactivity at concentrations of from about 0.01 millicurie (mCi) to 100 mCi per mL.

The imaging reagents provided by the present invention can be used for visualizing organs such as the kidney for diagnosing disorders in these organs, and tumors, in particular gastrointestinal tumors, myelomas, small cell lung carcinoma and other APUDomas, endocrine tumors such as medullary thyroid carcinomas and pituitary tumors, brain tumors such as meningiomas and astrocytomas, and tumors of the prostate, breast, colon, and ovaries can also be imaged. In accordance with this invention, the Tc-99m labeled peptide reagents are administered in a single unit injectable dose. The Tc-99m labeled peptide reagents provided by the invention may be administered intravenously in any conventional medium for intravenous injection such as an aqueous saline medium, or in blood plasma medium. Generally, the unit dose to be administered has a radioactivity of about 0.01 mCi to about 100 mCi, preferably 1 mCi to 20 mCi. The solution to be injected at unit dosage is from about 0.01 mL to about 10 mL. After intravenous administration, imaging in vivo can take place in a matter of a few minutes. However, imaging can take place, if desired, in hours or even longer, after the radiolabeled peptide is injected into a patient. In most instances, a sufficient amount of the administered dose will accumulate in the area to be imaged within about 0.1 of an hour to permit the taking of scintiphotos. Any conventional method of scintigraphic imaging for diagnostic purposes can be utilized in accordance with this invention.

The somatostatin receptor-binding linear peptides and non-radioactive metal complexes of the linear peptide reagents of the invention may be used clinically to promote regression of certain types of tumors, particularly those that express somatostatin receptors. The linear somatostatin analogue peptides of the invention can also be used to reduce the hormonal hypersecretion that often accompanies certain cancers, such as the APUDomas. Peptides of the invention used as therapeutic agents may be administered by any appropriate route, including intravenous, intramuscular or by mouth, and in any acceptable pharmaceutical carrier, in doses ranging from about 0.1 to about 49 mg/kg body weight/day.

This invention also provides peptides radiolabled with a cytotoxic radioisotope such as rhenium-186 or rhenium-188 that may be used for radiotherapy of certain tumors as described above. For this purpose, an amount of radioactive isotope from about 10 mCi to about 200 mCi may be administered via any suitable clinical route, preferably by intravenous injection.

The methods for making and labeling these compounds are more fully illustrated in the following Examples. These Examples illustrate certain aspects of the above-described method and advantageous results, and are shown by way of illustration and not limitation.

EXAMPLE 1

Solid Phase Peptide Synthesis

Solid phase peptide synthesis (SPPS) was carried out on a 0.25 millimole (mmole) scale using an Applied Biosystems Model 431A Peptide Synthesizer and using 9-fluorenylmethyloxycarbonyl (Fmoc) amino-terminus protection, coupling with dicyclohexylcarbodiimide/hydroxybenzotriazole or 2-(1H-benzotriazol-1-yl)-1,1,3,3-tetramethyluronium hexafluorophosphate/hydroxybenzotriazole (HBTU/HOBT), and using p-hydroxymethylphenoxymethylpolystyrene (HMP) resin for carboxyl-terminus acids or Rink amide resin for carboxyl-terminus amides.

Where appropriate, the following amino acid derivatives were synthesized. Homocysteine was prepared by alkaline hydrolysis of L-homocysteine lactone. Threoninol residues, wherein the carboxyl group of the amino acid is reduced to a primary alcohol, can be introduced into the peptides of the invention where appropriate using the procedure of Neugebauer et al. (1990, *Peptides: Proceedings of the 11th American Peptide Symposium*, pp. 1020–21). Fmoc. Hcy(Trt) and Fmoc.Pen(Trt) were prepared from the appropriate amino acids by tritylation with triphenylmethanol in TFA, followed by Fmoc derivitization as described by Atherton et al. (1989, *Solid Phase Peptide Synthesis*, IRL Press: Oxford). Fmoc.homohomocysteine(Trt) was prepared by reducing N,N-bis-Boc-glutamic acid-α-methyl ester with borane-THF, followed by mesylation and reaction with trityl-mercaptide, followed by removal of the Boc groups with $BF_3OEt$ in acetic acid, and then Fmoc derivitization as described above. $PhCH_2CHBrCOOH$ was prepared by treating phenylalanine (in a solution of water and TFA/saturated with NaBr) with sodium nitrite, followed by distillation to recover the pure product.

Where appropriate, 2-chloroacetyl, 2-bromoacetyl and 2-bromo-3-phenylpropionyl groups were introduced either by using the appropriate 2-halo acid as the last residue coupled during SPPS, or by treating the N-terminus free amino acid peptide bound to the resin with either 2-halo acid/diisopropylcarbodiimide/N-hydroxysuccinimide/NMP or 2-halo acid anhydride/diisopropylethylamine/NMP.

Where appropriate, HPLC-purified 2-haloacylated peptides were cyclized by stirring an 0.1–1.0 mg/mL solution in phosphate or bicarbonate buffer or dilute ammonium hydroxide (pH 8.0), optionally containing 0.5–1.0 mM EDTA, or acetonitrile or THF for 1–48 h followed optionally by acidification with acetic acid, lyophilization and HPLC purification.

Where appropriate, [BAM]($N^1,N^4$-bis(2-mercapto-2-methylpropyl)-1,4,10-triazadecane) was conjugated to the peptide by first activating the peptide carboxylate with a mixture of diisopropylcarbodiimide/N-hydroxysuccinimide or HBTU/HOBt in DMF, NMP or methylene chloride, followed by coupling in the presence of diisopropylethylamine. After coupling, the conjugates were deprotected as described above.

Where appropriate, BSME adducts were prepared by reacting single thiol-containing peptides (5 to 50 mg/mL in DMF buffered to pH 7 with N-methylmorpholine or N-ethyl-morpholine, or 50 mM sodium phosphate buffer, pH 7–8, optionally containing 0.5 mM EDTA or DMF or THF or acetonitrile) with 0.5 molar equivalents of BMME (bis-maleimidomethylether) pre-dissolved in acetonitrile at room temperature for approximately 1–18 hours. The solution was concentrated and the product was purified by HPLC.

Where appropriate, TSEA adducts were prepared by reacting single thiol-containing peptide (at concentrations of 10 to 100 mg/mL peptide in DMF buffered to pH 7 with N-methylmorpholine or N-ethylmorpholine, or 5 to 50 mg/mL peptide in 50 mM sodium phosphate, pH 7–8, optionally containing 0.5mM EDTA or DMF or THF or acetonitrile) with 0.33 molar equivalents of TMEA (tris(2-maleimidoethyl)amine) pre-dissolved in acetonitrile or DMF, with or without 1 molar equivalent of triethanolamine, at room temperature for approximately 1–18h. Such reaction mixtures containing adducts were concentrated and the adducts were then purified using HPLC.

Where appropriate, BAT-BS (N-[2-(N',N'-bis(2-succinimidoethyl) aminoethyl)]-$N^6,N^9$-bis (2-methyl-2-mercaptopropyl)-6,9-diazanonanamide) adducts were prepared by reacting single thiol-containing peptide (at concentrations of 2 to 50 mg/mL peptide in DMF buffered to pH 7 with N-methyl-morpholine or N-ethyl-morpholine, or in 50 mM sodium phosphate (pH 7–8), optionally containing 0.5 mM EDTA or DMF or THF or acetonitrile) with 0.5 molar equivalents of BAT-BM (N-[2-(N',N'-bis(2-maleimidoethyl)]aminoethyl)]-$N^9$-(t-butoxycarbonyl)-$N^6,N^9$-bis(2-methyl-2-triphenylmethylthiopropyl)-6,9-diazanonanamide) pre-dissolved in acetonitrile or THF, at room temperature for approximately 1–18 h. The solution was then evaporated to dryness and [BAT-BS]-peptide conjugates deprotected by treatment with 10mL TFA and 0.2 mL triethylsilane for 1 h. The solution was concentrated, the product adducts precipitated with ether, and then purified by HPLC.

Where appropriate, the [DTPA]moiety can be introduced using the method of Bakker et al. (1991,Life Sci. 49: 1583–1591,hereby incorporated by reference).

Resin-bound products were routinely cleaved using a solution of trifluoroacetic acid or trifluoroacetic acid and methylene chloride, optionally containing water, thioanisole, ethanedithiol, and triethylsilane, prepared in ratios of 100:5:5:2.5:2 for 0.5–3 h at room temperature. Crude peptides were purified by preparative high pressure liquid chromatography (HPLC) using a Waters Delta Pak C18 column and gradient elution using 0.1% trifluoroacetic acid (TFA) in water modified with acetonitrile. Acetonitrile was evaporated from the eluted fractions which were then lyophilized. The identity of each product was confirmed by fast atom bombardment mass spectroscopy (FABMS) or by electrospray mass spectroscopy (ESMS).

Somatostatin analogues synthesized as provided herein, as well as the products of such synthesis identified by FABMS, are shown in Table I below.

EXAMPLE 2

A General Method for Radiolabeling with Tc-99m 0.1 mg of a peptide prepared as in Example 2 was dissolved in 0.1 mL of water or 50/50 ethanol/water or phosphate-buffered saline or 50 mM potassium phosphate buffer (pH =5, 6 or 7.4). Tc-99m gluceptate was prepared by reconstituting a Glucoscan vial (E.I. DuPont de Nemours, Inc.) with 1.0 mL of Tc-99m sodium pertechnetate containing up to 200 mCi and allowed to stand for 15 minutes at room temperature. 25 µl of Tc-99m gluceptate was then added to the peptide and the reaction allowed to proceed at room temperature or at 100° C. for 15–30 min and then filtered through a 0.2 µm filter.

The Tc-99m labeled peptide purity was determined by HPLC using the following conditions: a Waters Delta Pak RP-18, 5µ, 4.6 mm×220 mm analytical column was loaded with each radiolabeled peptide, and the peptides eluted at a solvent flow rate equal to 1 mL/min. Gradient elution was performed beginning with 100% solvent A (0.1% $CF_3COOH/H_2O$) and ending with 100% solvent $B_{90}$ (0.1% $CF_3COOH/90\%$ $CH_3CN/H_2O$) over the course of 10–20 min.

Radioactive components were detected using an in-line radiometric detector linked to an integrating recorder. Tc-99m gluceptate and Tc-99m sodium pertechnetate elute between 1 and 4 minutes under these conditions, whereas the Tc-99m labeled peptides eluted after a much greater amount of time, as illustrated in Table I below.

TABLE I

| Peptide | MH+ | RCY (%) | $R_t$ (min) |
|---|---|---|---|
| $C_{Acm}GC_{Acm}GGGF_D.Cpa.YW_DKTFT$.amide | 1749 | 97[4] | 15.7[2] |
| [DPTA].$F_D$.Cpa.$YW_D$KTFT($\epsilon$-K)GC.amide | 1837 | 97[5] | 15.5[2] |
| ma.GGG$F_D$.Cpa.$YW_D$KTFT.amide | 1417 | 98[4] | 12.2[3] |
| Ac.$C_{Acm}GC_{Acm}F_D$.Cpa.$YW_D$KTFT.amide | 1619 | 75[4] | 17.1, 17.5[2] |
| $F_D$.Cpa.$YW_D$KTFT$C_{Acm}GC_{Acm}$.amide | 1577 | 93[3] | 12.1[3] |
| [DPTA].D-Nal.Cpa.$YW_D$KTFT($\epsilon$-K)GCKK.amide | 2143 | nd | nd |
| AKCGGG$F_D$.Cpa.$YW_D$KTFT.amide | 1612 | 98[5] | 15–16[2] |
| [DPTA].D-Nal.Cpa.$YW_D$KTFT($\epsilon$-K)GC.amide | 1887 | 97[5] | 16.2[2] |
| $F_D$.Cpa.$YW_D$KTFT.GGG$C_{Acm}GC_{Acm}$.amide | 1749 | 76[3] | 17.7, 18.0[1] |
| [DTPA].Aca.$F_D$.Cpa.$YW_D$KTFT($\epsilon$-K)GC.amide | 1950 | 97[2] | 11.5[3] |
| [DTPA].($\epsilon$-K)GC$F_D$.F$YW_D$KTFT.amide | 1802 | 97[2] | 11.5[3] |
| Ac.CGC$F_D$.Cpa.$YW_D$KTFT.amide | 1477 | 98[6] | 18.1[2] |
| $F_D$.Cpa.$YW_D$KTFTCGC.amide | 1435 | 99[6] | 16.8, 17.0[2] |
| [DTPA].(D-Nal.CY$W_D$KVCT)$_2$ | 2554 | 97[6] | 11.8–12.4[3] |
| Ac.$F_D$.F$YW_D$KTFT($\epsilon$-K)GC.amide | 1469 | 96[2] | 12.1, 12.6[3] |
| Ac.$F_D$F$YW_D$KTFTGGG($\epsilon$-K)GC.amide | 1640 | 98[2] | 11.9, 12.4[3] |
| $F_D$.Cpa.$YW_D$KTC.Nal.amide | 1224 | 88[6] | 18.6, 20.4[2] |
| K.[BAT].D-Nal.$C_{Me}YW_D$KV$C_{Me}$T.amide | 1573 | 97[6] | 12.5[3] |
| Ac.$F_D$F$YW_D$KTFGGG($\epsilon$-K)KC.amide | 1710 | 98[6] | 15.9[2] |
| Pic.G$C_{Acm}$GGG$F_D$.Cpa.$YW_D$KTFT.amide | 1681 | 98[6] | 13.8–16.8[1] |
| [DTPA].D-Nal.CY$W_D$KVCT.amide | 1473 | 97[6] | 11.0[3] |
| (2-ketogulonyl)-D-NalF$YW_D$KVCT.amide | 1318 | 98[2] | 12.4, 13.0[3] |
| $F_D$.Cpa.$YW_D$K.Abu.Nal.T($\epsilon$-K)GC.amide | 1495 | 95[5] | 16.5[2] |
| [DTPA].K.[BAT].D-Nal.$C_{Me}YW_D$KV$C_{Me}$T.amide | 1949 | 96[6] | 12.3[3] |
| $F_D$.Cpa.$YW_D$KTFT($\epsilon$-K)GC.amide | 1461 | 98[5] | 15.8[2] |
| [DTPA].$F_D$F$YW_D$KTFT($\epsilon$-K)GC.amide | 1801 | 97[3] | 11.3[3] |
| A$F_D$CF$W_D$KT$C_{Me}$T(CH$_2$OH) | 1106 | 99[1] | 11.3–11.9[3] |
| [DTPA].$F_D$GY$W_D$KTCT(CH$_2$OH) | nd | 96[2] | 10.6[1] |
| [DTPA].Nal.SY$W_D$KVTK.[BAT].amide | 1801 | 96[2] | 12.0[3] |
| [DPTA].Nal.SY$W_D$KVCT.amide | 1457 | 95[6] | 11.6[3] |

*The following labeling conditions were used with the appropriate peptides:
1. The peptide is dissolved in 50 mM potassium phosphate buffer (pH 7.4) and labeled at room temperature.
2. The peptide is dissolved in water and labeled at room temperature.
3. The peptide is dissolved in water and labeled at 100° C.
4. The peptide is dissolved in 50% ethanol/water and labeled at 100° C.
5. The peptide is dissolved in 10% hydroxypropylcyclodextrin and labeled at room temperature.
6. The peptide is dissolved in 50% ethanol/water labeled at room temperature.

**HPLC methods:
general:
solvent A = 0.1% CF3COOH/H$_2$O
solvent B$_{90}$ = 0.1% CF$_3$COOH/90% CH$_3$CN/H$_2$O
solvent flow rate = 1 mL/min
Vydak column = Vydak 218TP54 RP-18, 5μ × 220 mm × 4.6 mm analytical column with guard column
Waters column = Waters Delta-Pak C18, 5 μm, 39 × 150 mm
Method 1:  Vydak column    100% A to 100% B$_{90}$ in 10 min
Method 2:  Waters column   100% A to 100% B$_{90}$ in 20 min
Method 3:  Waters column   100% A to 100% B$_{90}$ in 10 min
Single-letter abbreviations for amino acids can be found in G. Zubay, Biochemistry (2d. ed.), 1988 (MacMillen Publishing: New York) p. 33; Ac = acetyl; Acm = acetamidomethyl; ma = mercaptoacetic acid; Aca = 6-aminocaproic acid; Hly = homolysine; Apc = L-[S—(3-aminopropyl)cysteine; $F_D$ = D-phenylalanine; $W_D$ = D-tryptophan; $Y_D$ = D-tyrosine; Cpa = L—(4-chlorophenyl)alanine; D-Nal =D-2-naphthylalanine; Nle = norleucine; Hcy = homocysteine; Hhc = homohomocysteine; Pen = penicillamine; Aib = aminoisobutyric acid; Nal = 2-naphthylalanine; D-Nal = D-2-naphthylalanine; Ain = 2-aminoindane-2-carboxylic acid; Achxa = 4-amino-cyclohexylalanine; Amf = 4-aminomethyl-phenylalanine; Aec = S—(2-aminoethyl)cysteine; Apc = S—(3-aminopropyl)cysteine; Aes = O—(2-aminoethyl)serine; Aps = O—(3-aminopropyl)serine; Abu = 2-aminobutyric acid; Nva = norvaline; T(CH$_2$OH) = threoninol (on which the carboxylic acid moiety has been reduced to a primary alcohol); $\epsilon$-K = a lysine residue in a peptide in which the peptide bond involves the $\epsilon$-amino group on the lysine sidechain rather than the α-amino group; Pic = picolinoyl (pyridine-2-carbonyl); Pica = picolylamine (2-(aminomethyl)pyridine); BAT = N$^6$,N$^9$-bis(2-mercapto-2-methylpropyl)-6,9-diazanonanoic acid; BAT (protected) = N$^9$-(t-butoxycarbonyl)-N$^6$,N$^9$-bis(2-methyl-2-triphenylmethylthiopropyl)-6,9-diazanonanoicacid; BAM = N$^1$,N$^4$-bis(2-mercapto-2-methylpropyl)-1,4,10-triazadecane; BAM (protected) = N$^1$-(t-butoxycarbonyl)-N$^1$,N$^4$-bis(2-methyl-2-triphenylmethylthiopropyl)-1,4,10-triazadecane; [BAT- BM] = N-[2-(N',N'-bis(2-maleimidoethyl)aminoethyl]-N$^9$-(t-butoxycarbonyl)-N$^6$,N$^9$-bis(2-methyl-2-triphenylmethylthiopropyl)-6,9-diazanonanamide; [BAT-BS] = N-[2-(N',N'-bis(2-succinimidoethyl)aminoethyl]-N$^6$,N$^9$-bis(2-mercapto-2-methylpropyl)-6,9-diazanonanamide; [BMME] = bis-maleimidomethylether; [BSME] = bis-succinimidomethylether; [DTPA] =diethylenetriaminepentaacetic acid.
RCY (%) = radiochemical yield (determined by HPLC)

EXAMPLE 3

Inhibition of Binding of [$^{125}$I-Tyr$^{11}$]somatostatin-14 to AR42J Rat Pancreatic Tumor Cell Membranes The ability of various somatostatin analogues of the invention to bind to somatostatin receptors in vitro was demonstrated by assaying the ability of such analogues to inhibit binding of a radiolabeled somatostatin analogue to somatostatin receptor-containing cell membranes. The rat pancreatic tumor cell line AR42J which expresses the somatostatin receptor was cultured in Dulbecco's minimal essential media (DMEM) supplemented with 10% fetal bovine serum (FBS) and 8 mM glutamine in a humdified 5% $CO_2$ atmosphere at 37° C. in T-flasks. Harvested cells were homogenized in cold 50 mM Tris-HCl buffer (pH 7.4) and the homogenate then centrifuged at 39,000 g for 10 min at 4° C. Pellets were washed once with buffer and then resuspended in an ice-cold solution of 10 mM Tris-HCl (pH 7.4). Equal aliquots of this cell membrane preparation were incubated with [$^{125}$I-Tyr$^{11}$]somatostatin-14 (at a final concentration of 0.5nM and 750,000 cpm/mL, at a specific activity of 2000 Ci/mmol, Amersham, Arlington Heights, Ill.) and peptide at a final concentration of from $10^{-11}$ M to $10^{-6}$ M in a solution of 50 mM HEPES (pH 7.4) containing 1% bovine serum albumin (BSA), 5 mM $MgCl_2$, Trasylol (200,000 International Units), bacitracin (0.02 mg/mL) and phenylmethylsulfonylfluoride (0.02 mg/mL) for 25 min at 30° C. Using a filtration manifold, this mixture was filtered through a polyethyleneimine-washed GC/F filter (Whatman, Maidstone, England), and the residue remaining on the filter wastled thrice with 5 mL cold HEPES buffer. The filter and a sample of the filter washings were then counted in a gamma counter. To assess non-specific binding, the assay was performed in the presence of unlabeled somatostatin-14 at 200 nM. Data analysis including Hill plots of the data provided inhibition constants (see Bylund & Yamamura, "Methods of receptor binding", in *Methods in Neurotransmitter Receptor Analysis*, Yamamura et al., eds., Raven Press: New York, 1990).

These results are presented in the following Table. The data show that the peptides of the instant invention have a high affinity of binding for somatostatin receptors.

TABLE II

| Peptide | MH$^+$ | $K_i$ (nM) |
|---|---|---|
| $C_{Acm}GC_{Acm}GGGF_D.Cpa.YW_DKTFT.amide$ | | <0.01 |
| [DTPA].$F_D$.CPa.YW$_D$KTFT($\epsilon$-K)GC.amide | | 0.24 |
| maGGGF$_D$.Cpa.YW$_D$KTFT.amide | | 0.25 |
| Ac.C$_{Acm}$GC$_{Acm}$F$_D$.CPa.YW$_D$KTFT.amide | | 0.73 |
| F$_D$.CPa.YW$_D$KTFTC$_{Acm}$GC$_{Acm}$.amide | | 0.85 |
| [DTPA].D-Nal.Cpa.YW$_D$KTFT($\epsilon$-K)GCKK.amide | | 1.3 |
| AKCGGGF$_D$.Cpa.YW$_D$KTFT.amide | | 1.4 |
| [DTPA].D-Nal.Cpa.YW$_D$KTFT($\epsilon$-K)GC.amide | | 2.0 |
| F$_D$.Cpa.YW$_D$KTFT.GGGC$_{Acm}$GC$_{Acm}$.amide | | 2.4 |
| [DTPA].Aca.F$_D$.Cpa.YW$_D$KTFT($\epsilon$-K)GC.amide | | 2.6 |
| [DTPA].($\epsilon$-K)GCF$_D$.FYW$_D$KTFT.amide | | 3.3 |
| Ac.CGCF$_D$.Cpa.YW$_D$KTFT.amide | | 4.4 |
| F$_D$.Cpa.YW$_D$KTFTCGC.amide | | 4.8 |
| [DTPA].(D-Nal.CYW$_D$KVCT)$_2$ | | 7.2 |
| Ac.F$_D$.FYW$_D$KTFT($\epsilon$-K)GC.amide | | 7.9 |
| Ac.F$_D$FYW$_D$KTFTGGG($\epsilon$-K)GC.amide | | 8.2 |
| F$_D$.Cpa.YW$_D$KTC.Nal.amide | | 8.2 |
| K.[BAT].D-Nal.C$_{Me}$YW$_D$KVC$_{Me}$T.amide | | 9.9 |
| [Re=O]-complexed Peptides | | |
| [DTPA].D-Nal.Cpa.YW$_D$KTFT($\epsilon$-K)GC.amide | 2085 | 0.007 |
| [DTPA].F$_D$.Cpa.YW$_D$KTFT($\epsilon$-K)GC.amide | 2036 | 0.027 |
| F$_D$.Cpa.YW$_D$KTFT($\epsilon$-K)GC.amide | nd | 0.36 |
| F$_D$.CPa.YW$_D$KTFTCGC.amide | 1635 | 0.37 |
| C$_{Acm}$GC$_{Acm}$GGGF$_D$.Cpa.YW$_D$KTFT.amide | 1807 | 0.43 |
| AKCGGGF$_D$.Cpa.YW$_D$KTFT.amide | 1812 | 0.76 |
| maGGGF$_D$.Cpa.YW$_D$KTFT.amide | 1618 | 0.97 |
| Ac.F$_D$FYW$_D$KTFT($\epsilon$-K)GC.amide | 1688 | 1.5 |
| AKCGGGF$_D$FYW$_D$KTFT.amide | 1812 | 2.9 |
| F$_D$.Cpa.YW$_D$K.Abu.Nal.T($\epsilon$-K)GC.amide | 1695 | 3.3 |
| Ac.CGCF$_D$.Cpa.YW$_D$KTFT.amide | 1677 | 4.1 |
| Ac.F$_D$FYW$_D$KTFGGG($\epsilon$-K)KC.amide | 1911 | 6.1 |
| Ac.F$_D$FYW$_D$KTFTGGG($\epsilon$-K)GC.amide | 1840 | 8.1 |
| [DTPA].Aca.F$_D$.Cpa.YW$_D$KTFT($\epsilon$-K)GC.amide | 2149 | 8.2 |

It should be understood that the foregoing disclosure emphasizes certain specific embodiments of the invention and that all modifications or alternatives equivalent thereto are within the spirit and scope of the invention as set forth in the appended claims.

What is claimed is:

1. A composition of matter that is linear somatostatin receptor-binding peptide reagent having the formula:

$$X^1-A^1A^2-B^1B^2B^3B^4-C^1C^2-X^2$$

wherein

X$^1$ and X$^2$ are each independently hydrophilic moieties wherein X$^1$ is an amino acid, or a peptide having an amino acid sequence of no more than 10 residues, or a monosaccharide, or an oligosaccharide comprising 10 or fewer saccharide units, or a polyoxyanion, and X$^2$ is a polyoxyanion, or an amino acid, or a peptide having an amino acid sequence of no more than 10 residues (including peptides wherein the carboxyl group of the carboxyl-terminal amino acid is reduced to an alcohol), or a monosaccharide or an oligosaccharide comprising 10 or fewer saccharide units;

$A^1$, $A^2$ and $C^1$ are each independently a lipophilic D- or L-amino acid, or S-alkylated cysteine, penicillamine, homocysteine or homohomocysteine;

$B^1$ is D- or L-Phe, or D- or L-Tyr, or D- or L-Nal, or Ain or substituted derivatives thereof;

$B^2$ is D- or L-Trp or substituted derivatives thereof;

$B^3$ is D- or L-Lys, or Hly, Achxa, Amf, Aec, Apc, Aes, Aps or substituted derivatives thereof;

$B^4$ and $C^2$ are each independently D- or L-Thr, Ser, Val, Phe, Ile, Abu, Nle, Leu, Nva, Nal or Aib or substituted derivatives thereof; and wherein the somatostatin receptor-binding peptide reagent does not comprise a radiolabel chelating moiety.

2. The composition of matter of claim 1 wherein $B^1$ is phenylalanine or tyrosine, $B^2$ is D-tryptophan, $B^3$ is lysine and $B^4$ is threonine or valine.

3. The composition of matter of claim 1 further comprising a polyvalent linking moiety that is covalently linked to a multiplicity of the somatostatin receptor-binding peptides to form a multimeric polyvalent somatostatin receptor binding agent, wherein the molecular weight of the multimeric polyvalent somatostatin receptor binding agent is less than about 20,000 daltons.

4. The composition of matter of claim 3 wherein the polyvalent linking moiety is bis-succinimidylmethylether, 4-(2,2-dimethylacetyl)benzoic acid, N-[2-(N',N'-bis(2-succinimidoethyl)aminoethyl)]-$N^6$, $N^9$-bis(2-methyl-2-mercaptopropyl)-6,9-diazanonanamide, tris(succinimidylethyl)amine or a derivative thereof.

5. The composition of matter of claim 1 wherein the somatostatin receptor-binding peptide is chemically synthesized in vitro.

6. The composition of matter of claim 5 wherein the somatostatin receptor-binding peptide is synthesized by solid phase peptide synthesis.

7. A method for alleviating a somatostatin-related disease in an animal comprising administering a therapeutically effective amount of the somatostatin receptor binding peptide of claim 1 to the animal.

8. The method of claim 7 wherein the animal is a human.

9. A composition of matter that is a linear somatostatin receptorbinding peptide reagent having the formula:

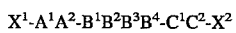

wherein $X^1$ is H, lower alkyl or substituted alkyl, aryl or substituted aryl, alkanoyl or substituted alkanoyl, aroyl or substituted aroyl, or a hydrophilic moiety;

$A^1$, $A^2$ and $C^1$ are each independently a lipophilic D- or L-amino acid, or S-alkylated cysteine, penicillamine, homocysteine or homohomocysteine;

$B^1$ is D- or L-Phe, or D- or L-Tyr, or D- or L-Nal, or Ain or substituted derivatives thereof;

$B^2$ is D- or L-Trp or substituted derivatives thereof;

$B^3$ is D- or L-Lys, or Hly, Achxa, Amf, Aec, Apc, Aes, Aps or substituted derivatives thereof;

$B^4$ and $C^2$ are each independently D- or L-Thr, Ser, Val, Phe, Ile, Abu, Nle, Leu, Nva, Nal or Aib or substituted derivatives thereof;

$X^2$ is —COOR$^9$, —CH$_2$OH, CH$_2$COOR$^9$, or —CON(R$^9$)$_2$, where each R$^9$ is independently H, lower linear or cyclic alkyl or substituted derivatives thereof or substituted with a hydrophilic moiety;

and wherein the somatostatin receptor binding peptide is covalently linked to a radiolabel-binding moiety, wherein the radiolabel-binding moiety is not covalently linked to the moieties $B^1$, $B^2$, $B^3$ or $B^4$ of the peptide and wherein the radiolabel binding moiety is capable of binding Tc-99m, Re-186 or Re-188.

10. The composition of matter of claim 9 wherein $X^1$ is a an amino acid, or a peptide having an amino acid sequence of no more than 10 residues, or a monosaccharide, or an oligosaccharide comprising 10 or fewer saccharide units, or a polyoxyanion and $X^2$ is a polyoxyanion, or an amino acid, or an amino acid, or a peptide having an amino acid sequence of no more than 10 residues, or a monosaccharide, or an oligosaccharide comprising 10 or fewer saccharide units.

11. The composition of matter of claim 9 wherein $B^1$ is phenylalanine or tyrosine, $B^2$ is D-otryptophan, $B^3$ is lysine and $B^4$ is threonine or valine.

12. The composition of matter of claim 9 wherein the reagent further comprises a polyvalent linking moiety covalently linked to a multiplicity of the somatostatin receptor binding peptides and also covalently linked to a multiplicity of radiolabelbinding moleties to comprise a reagent for preparing a multimeric polyvalent somatostatin receptor binding reagent, wherein the molecular weight of the multimeric polyvalent somatostatin receptor binding reagent is less than about 20,000 daltons.

13. The composition of matter of claim 12 wherein the polyvalent linking moiety is bis-succinimidylmethylether, 4-(2,2-dimethylacetyl)benzoic acid, N-[2-(N',N'-bis(2-succinimidethy)aminethy)]-$N^6$,$N^9$-bis(2-methyl-2-mercaptprpy)-6,9-diazanonanamide, tris(succinimidylethyl)amine or a derivative thereof.

14. A scintigraphic imaging agent comprising the composition of matter of claim 9 radiolabeled with technetium-99m.

15. A radiotherapeutic agent comprising the composition of matter of claim 9 radiolabeled with a cytotoxic radioisotope selected from the group consisting of rhenium-186 and rhenium-188.

16. A complex formed by reacting the composition of matter of claim 9 with technetium-99m in the presence of a reducing agent.

17. The complex of claim 16, wherein the reducing agent is selected from the group consisting of a dithionite ion, a stannous ion and a ferrous ion.

18. A complex formed by labeling the composition of matter of claim 9 with technetium-99m by ligand exchange of a prereduced technetium-99m complex.

19. A composition comprising the composition of matter of claim 9 and a stannous ion.

20. A kit for preparing a radiopharmaceutical preparation, said kit comprising a sealed vial containing a predetermined quantity of the composition of matter of claim 9 and a sufficient amount of reducing agent to label the reagent with technetium-99m.

21. A method for labeling a composition of matter according to claim 9 comprising reacting the composition of matter with technetium-99m in the presence of a reducing agent.

22. The method of claim 21, wherein the reducing agent is selected from the group consisting of a dithionite ion, a stannous ion and a ferrous ion.

23. A composition of matter according to claim 9 wherein the somatostatin receptor-binding peptide is chemically synthesized in vitro.

24. A composition of matter according to claim 23 wherein the somatostatin receptor-binding peptide is synthesized by solid phase peptide synthesis.

25. A composition of matter according to claim 23 wherein the radiolabel-binding moiety is covalently linked to the somatostatin receptor-binding peptide during in vitro chemical synthesis.

26. A composition of matter according to claim 25 wherein the radiolabel-binding moiety is covalently linked to the somatostatin receptor-binding peptide during solid phase peptide synthesis.

27. A reagent for preparing a scintigraphic imaging agent for imaging sites within a mammalian body comprising a composition of matter according to claim 9 that is a somatostatin receptor-binding peptide and a radiolabel-binding moiety covalently linked thereto, the radiolabel-binding moiety having the formula:

$$C(pgp)^s\text{-}(aa)\text{-}C(pgp)^s$$

wherein $(pgp)^s$ is H or a thiol protecting group and (aa) is an amine acid; or $$A\text{-}CZ(B)\text{-}[C(R'R'')]_n\text{-}X$$

wherein

A is H, HOOC, $H_2$NOC, (peptide)-NHOC, (peptide)-OOC or R'''';

B is H, SH, -NHR''', -N(R''')-(peptide), or R'''';

X is H, SH, -NHR''', -N(R''')-(peptide) or R'''';

Z is H or R'''';

R', R'', R''' and R'''' are independemly H or lower straight or branched chain or cyclic alkyl;

n is 0, 1 or 2;

and where B is -NHR''' or -N(R''')-(peptide), X is SH, and n is 1 or 2;

where X is -NHR''' or -N(R''')-(peptide), B is SH, and n is 1 or 2;

where B is H or R'''', A is HOOC, $H_2$NOC, (peptide)-NHOC, (peptide)-OOC, X is SH, and n is 0 or 1;

where A is H or R'''', then where B is SH, X is -NHR''' or-N(R''')-(peptide) and where X is SH, B is -NHR'''or-N(R''')-(peptide);

where X is H or R'''', A is HOOC, $H_2$NOC, (peptide)-NHOC, (peptide)-OOC and B is SH;

where Z is methyl, X is methyl, A is HOOC, $H_2$NOC, (peptide)-NHOC, (peptide)-OOC, B is SH and n is 0;

where B is SH and X is SH, n is not 0; or

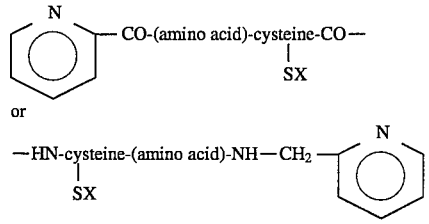

wherein
X=H or a protecting group;
(amino acid)=any amino acid; or

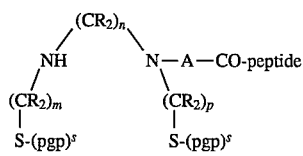

wherein
each R is independently H, $CH_3$ or $C_2H_5$;
each $(pgp)^s$ is independently a thiol protecting group or H;
m, n and p are independently 2 or 3;
A=linear or cyclic lower alkyl, aryl, heterocyclyl, combinations or substituted
derivatives thereof;

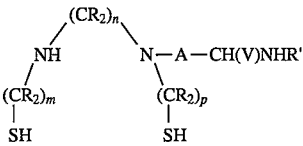

wherein
each R is independently H, $CH_3$ or $C_2H_5$;
m, n and p are independently 2 or 3;
A=linear or cyclic lower alkyl, aryl, heterocyclyl, combinations or substituted
derivatives thereof;
V=H or –CO-peptide;
R'=H or peptide;
and wherein when V=H, R'=peptide and when R'=H, V=–CO-peptide; wherein each R is independently H, lower alkyl having 1 to 6 carbon atoms, phenyl, or phenyl substituted with lower alkyl or lower alkoxy, and wherein each n is independently 1 or 2.

28. The reagent of claim 27 wherein the cysteine of the radiolabel-binding moiety having formula $$C(pgp)\text{-}(aa)\text{-}C(pgp)^s$$

has a protecting group of the formula $$-CH_2\text{-}NH\text{-}CO\text{-}R$$

wherein R is a lower alkyl having 1 to 6 carbon atoms, 2-,3-,4-pyridyl, phenyl, or phenyl substituted with lower alkyl, hydroxy, lower alkoxy, carboxy, or lower alkoxycarbonyl.

29. The reagent of claim 32 wherein the radiolabel-binding moiety $C(pgp)^s$-(aa)-$C(pgp)^s$ has the formula:

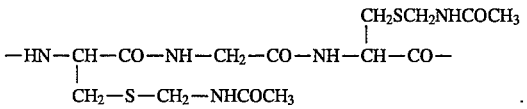

30. A scintigraphic imaging agent that is the reagent of claim 27 radiolabeled with technetium-99m.

31. A complex formed by reacting the reagent of claim 27 with technetium-99m in the presence of a reducing agent.

32. The complex of claim 31, wherein the reducing agent is selected from the group consisting of a dithionite ion, a stannous ion and a ferrous ion.

33. A complex formed by labeling the reagent of claim 27 with technetium-99m by ligand exchange of a prereduced technetium-99m complex.

34. A composition comprising the reagent of claim 27 and a stannous ion.

35. A kit for preparing a radiopharmaceutical preparation, said kit comprising a sealed vial containing a predetermined quantity of the reagent of claim 27 and a sufficient amount of reducing agent to label the reagent with technetium-99m.

36. A method for labeling a reagent according to claim 27 comprising reacting the reagent with technetium-99m in the presence of a reducing agent.

37. The method of claim 36, wherein the reducing agent is selected from the group consisting of a dithionite ion, a stannous ion and a ferrous ion.

38. A method for imaging a site within a mammalian body comprising administering an effective diagnostic amount of the reagent of claim 30 and detecting the technetium-99m localized at the site in the mammalian body.

39. The reagent according to claim 27 wherein the somatostatin receptor-binding peptide comprising the reagent is chemically synthesized in vitro.

40. The reagent according to claim 39 wherein the somatostatin receptor-binding peptide is synthesized by solid phase peptide synthesis.

41. The reagent according to claim 39 wherein the radiolabel-binding moiety is covalently linked to the somatostatin receptor-binding peptide during in vitro chemical synthesis.

42. The reagent according to claim 41 wherein the radiolabel-binding moiety is covalently linked to the somatostatin receptor-binding peptide during solid phase peptide synthesis.

43. The reagent of claim 27 wherein the reagent further comprises a polyvalent linking moiety covalently linked to a multiplicity of the somatostatin receptor binding peptides and also covalently linked to a multiplicity of radiolabel-binding moieties to comprise a reagent for preparing a multimeric polyvalent somatostatin receptor binding reagent, wherein the molecular weight of the multimeric polyvalent somatostatin receptor binding reagent is less than about 20,000 daltons.

44. The reagent of claim 43 wherein the polyvalent linking moiety is bis-succinimidylmethylether, 4-(2,2-dimethylacetyl)benzoic acid, N-[2-(N',N'-bis(2-succinimidethyl)aminethyl) ]-$N^6$,$N^9$-bis(2-methyl-2-mercaptopropyl)-6,9-diazannanamide, tris(succinimidylethyl)amine or a derivative thereof.

45. A composition of matter according to claim 9 wherein the radiolabel binding moiety forms a neutral complex with technetium-99m.

46. A composition of matter according to claim 9 radiolabeled with technetium-99m.

47. A composition of matter according to claim 9 radiolabeled with a radioisotope selected from the group consisting of, rhenium-186 and rhenium-188.

48. A composition of matter comprising a somatostatin receptor-binding peptide reagent selected from the group consisting of reagents having the formula:
$C_{Acm}GC_{Acm}GGGF_D$.Cpa.YW$_D$KTFT.amide
[DTPA].F$_D$.Cpa.YW$_D$KTFT($\epsilon$-K)GC.amide
ma. GGGF$_D$.Cpa.YW$_D$KTFT.amide
Ac.C$_{Acm}$GC$_{Acm}$F$_D$.Cpa.YW$_D$KTFT.amide
F$_D$.Cpa.YW$_D$KTFTC$_{Acm}$GC$_{Acm}$.amide
[DTPA].D-Nal.Cpa.YW$_D$KTFT($\epsilon$-K)GC.amide
AKCGGGF$_D$.Cpa.YW$_D$KTFT.amide      [DTPA].D-Nal-.Cpa.YW$_D$KTFT($\epsilon$-K)GC.amide
F$_D$.Cpa.YW$_D$KTFT.GGGC$_{Acm}$GC$_{Acm}$.amide
[DTPA].Aca.F$_D$.Cpa.YW$_D$KTFT($\epsilon$-K)GC.amide
[DTPA].($\epsilon$-K)GCF$_D$.FYW$_D$KTFT.amide
Ac.CGCF$_D$.Cpa.YW$_D$KTFT.amide
F$_D$.Cpa.YW$_D$KTFTCGC.amide
[DTPA].(D-Nal.CYW$_D$KVCT)$_2$
Ac.F$_D$.FYW$_D$KTFT($\epsilon$-K)GC.amide
Ac.F$_D$FYW$_D$KTFTGGG($\epsilon$-K)GC.amide
C$_{Acm}$GC$_{Acm}$GGGF$_D$.Cpa.YW$_D$KTFT.amide
F$_D$.Cpa.YW$_D$KTC.Nal.amide
K.[BAT].D-Nal. C$_{Me}$YW$_D$KVC$_{Me}$T.amide
Ac.F$_D$FYW$_D$KTFGGG($\epsilon$-K)KC.amide
Pic.GC$_{Acm}$GGGF$_D$.Cpa.YW$_D$KTFT.amide [DTPA].D-Nal-.CYW$_D$KVCT.amide (2-ketogulonyl)-D-NalFYW$_D$KVCT.amide
F$_D$.Cpa.YW$_D$K.Abu.Nal.T($\epsilon$-K)GC.amide
[DTPA].K.[BAT].D-Nal.C$_{Me}$YW$_D$KVC$_{Me}$T.amide
F$_D$.Cpa.YW$_D$KTFT($\epsilon$-K)GC.amide
[DTPA].F$_D$FYW$_D$KTFT($\epsilon$-K)GC.amide
AF$_D$CFW$_D$KTC$_{Me}$T(CH$_2$OH)
[DTPA].F$_D$GYW$_D$KTCT (CH$_2$OH)
[DTPA].Nal.SYW$_D$KVTK.[BAT]. amide
[DTPA].Nal.SYW$_D$KVCT.amide.

49. The composition of matter of claim 48 radiolabeled with technetium-99m.

50. The composition of matter of claim 48 radiolabeled with a radioisotope selected from the group consisting of rhenium-186 and rhenium-188.

51. A method for alleviating a somatostatin-related disease in an animal comprising administering a therapeutically effective amount of the composition of matter of claim 1 to the animal.

52. The method of claim 51 wherein the animal is a human.

53. The method of claim 51 wherein the therapeutically effective amount of the composition of matter administered to the animal is from about 0.1 to about 49 mg/kg body weight/day.

54. A method for alleviating a somatostatin-related disease in an animal comprising administering a therapeutically effective amount of the radiotherapeutic agent of claim 15 to the animal.

55. The method of claim 54 wherein the animal is a human.

56. The method of claim 54 wherein the therapeutically effective amount of the radiotherapeutic agent administered to the animal is from about 10 to about 200 mCi.

57. A pharmaceutical composition comprising the radiotherapeutic agent of claim 15 in a pharmaceutically-acceptable carrier.

58. A pharmaceutical composition comprising a composition of matter according to claim 1 that is a somatostatin receptor binding peptide in a pharmaceutically acceptable carrier.

59. A complex formed by reacting the composition of matter of claim 9 with a non-radioactive metal.

60. The complex of claim 59 wherein the non-radioactive metal is rhenium.

61. A complex formed by reacting the composition of matter of claim 12 with a non-radioactive metal.

62. The complex of claim 59 wherein the non-radioactive metal is rhenium.

63. A complex formed by reacting the composition of matter of claim 27 with a non-radioactive metal.

64. The complex of claim 63 wherein the non-radioactive metal is rhenium.

65. A complex formed by reacting the composition of matter of claim 43 with a non-radioactive metal.

66. The complex of claim 38 wherein the non-radioactive metal is rhenium.

67. A complex formed by reacting the composition of matter of claim 48 with a non-radioactive metal.

68. The complex of claim 67 wherein the non-radioactive metal is rhenium.

* * * * *